United States Patent
Straslicka et al.

(10) Patent No.: US 9,687,257 B2
(45) Date of Patent: Jun. 27, 2017

(54) PIN WIRE DRIVER DEVICE

(71) Applicant: Zimmer Surgical, Inc., Dover, OH (US)

(72) Inventors: Bruce Straslicka, Medina, OH (US); Mark Mahaffey, New Philadelphia, OH (US); Kévin Sornay, Meythet (FR); Marc Détry, Ayze (FR)

(73) Assignee: Zimmer Surgical, Inc., Dover, OH (US)

( * ) Notice: Subject to any disclaimer, the term of this patent is extended or adjusted under 35 U.S.C. 154(b) by 514 days.

(21) Appl. No.: 14/296,013

(22) Filed: Jun. 4, 2014

(65) Prior Publication Data

US 2015/0351820 A1  Dec. 10, 2015

(51) Int. Cl.
*A61B 17/16* (2006.01)
*A61B 17/88* (2006.01)
*F16D 1/104* (2006.01)
*A61B 17/00* (2006.01)

(52) U.S. Cl.
CPC ........ *A61B 17/1697* (2013.01); *A61B 17/162* (2013.01); *A61B 17/1624* (2013.01); *A61B 17/8897* (2013.01); *F16D 1/104* (2013.01); *A61B 2017/00477* (2013.01)

(58) Field of Classification Search
CPC ............ A61B 17/1697; A61B 17/8897; A61B 17/162; A61B 17/164
See application file for complete search history.

(56) References Cited

U.S. PATENT DOCUMENTS

| | | |
|---|---|---|
| 3,975,032 A | 8/1976 | Bent et al. |
| 4,736,742 A | 4/1988 | Alexson et al. |
| 5,553,675 A | 9/1996 | Pitzen et al. |
| 5,634,933 A | 6/1997 | McCombs et al. |
| 5,658,304 A | 8/1997 | Lim |
| 5,676,680 A | 10/1997 | Lim |
| 5,729,904 A | 3/1998 | Trott |
| 5,735,535 A | 4/1998 | McCombs et al. |
| 5,743,456 A | 4/1998 | Jones et al. |
| 5,747,953 A | 5/1998 | Philipp |

(Continued)

FOREIGN PATENT DOCUMENTS

WO WO-2010028001 A2 3/2010

OTHER PUBLICATIONS

"European Application Serial No. 15170717.1, Extended European Search Report mailed Mar. 18, 2016", 10 pgs.

*Primary Examiner* — Andrew Yang
(74) *Attorney, Agent, or Firm* — Schwegman Lundberg & Woessner, P.A.

(57) ABSTRACT

An instrument for facilitating the insertion of a pin or wire into a bone or other structure. The instrument includes a body, a first shaft and a second shaft at least partially positioned within the body, an actuator in communication with the second shaft, a first holding feature, and a second holding feature. The first shaft may include a lumen about a longitudinal axis, with the first shaft being rotatable about the longitudinal axis. The second shaft may be axially mobile and may be positioned at least partially around the first shaft. The first holding feature may be located adjacent a first position along the longitudinal axis and may be able to passively apply a first force to an elongated member received in the lumen. The second holding feature may be capable of applying a second force to the elongated member received in the lumen.

20 Claims, 8 Drawing Sheets

(56) References Cited

U.S. PATENT DOCUMENTS

| | | |
|---|---|---|
| 5,794,715 A | 8/1998 | Norman |
| 5,833,246 A | 11/1998 | Trott |
| 5,833,704 A | 11/1998 | McCombs et al. |
| 5,839,196 A | 11/1998 | Trott |
| 5,902,306 A | 5/1999 | Norman |
| 5,941,891 A | 8/1999 | Walen et al. |
| 5,961,532 A | 10/1999 | Finley et al. |
| 5,993,454 A | 11/1999 | Longo |
| 6,017,354 A | 1/2000 | Culp et al. |
| 6,042,585 A | 3/2000 | Norman |
| 6,045,564 A | 4/2000 | Walen et al. |
| 6,050,989 A | 4/2000 | Fox et al. |
| 6,090,123 A | 7/2000 | Culp et al. |
| 6,139,228 A | 10/2000 | Longo |
| 6,520,969 B2 | 2/2003 | Lambrecht et al. |
| 6,736,829 B1 | 5/2004 | Li et al. |
| 6,752,816 B2 | 6/2004 | Culp et al. |
| 6,786,897 B2 | 9/2004 | Mc Ie et al. |
| 6,917,183 B2 | 7/2005 | Barlev et al. |
| 6,958,071 B2 | 10/2005 | Carusillo et al. |
| 6,960,894 B2 | 11/2005 | Carusillo et al. |
| 7,041,120 B2 | 5/2006 | Li et al. |
| 7,237,990 B2 | 7/2007 | Deng |
| 7,422,594 B2 | 9/2008 | Zander et al. |
| RE40,681 E | 3/2009 | Pitzen et al. |
| 7,501,190 B2 | 3/2009 | Ise |
| 7,517,351 B2 | 4/2009 | Culp et al. |
| 7,638,958 B2 | 12/2009 | Philipp et al. |
| 7,682,333 B2 | 3/2010 | Deng |
| 7,717,931 B2 | 5/2010 | Himes |
| 7,981,114 B2 | 7/2011 | Zander et al. |
| 7,998,157 B2 | 8/2011 | Culp et al. |
| 8,035,487 B2 | 10/2011 | Malackowski |
| 8,137,370 B2 | 3/2012 | Deng |
| 8,419,760 B2 | 4/2013 | Wiebe, III |
| 2003/0023256 A1 | 1/2003 | Estes et al. |
| 2006/0053974 A1 | 3/2006 | Blust et al. |
| 2013/0060278 A1 | 3/2013 | Bozung et al. |

PIN WIRE DRIVER DEVICE

TECHNICAL FIELD

The disclosure is directed to medical devices for use in surgery. More particularly, the disclosure is directed to surgical instruments for driving elongated pins or wires into bones and/or other structures.

BACKGROUND

When attaching pins and/or wires to a bone of a patient, medical professionals may need to perform drilling, tapping, and/or screwing steps. When performing these tasks, powered surgical instruments may be utilized for driving elongated pins and/or wires. Powered surgical instruments used for driving elongated pins and/or wires may typically comprise a hand piece that drives a cannulated shaft through which a pin or wire may be passed. A drive shaft of the powered surgical instrument receiving the pin and/or wire may rotate, which in-turn rotates the received pin and/or wire in order to advance the pin and/or wire extending from the drive shaft into a bone structure or other structure. While pins usually have larger diameters than wires, for purposes of this description, the term "pins" and "wires" may be considered interchangeable.

SUMMARY

The disclosure is directed to several alternative or complementary designs, materials, and methods of using medical device structures and assemblies. Although it is noted that conventional surgical instruments for driving a wire or pin into bone exist, there is an ongoing need for improvement on those devices.

Accordingly, an illustrative embodiment of the disclosure is an instrument for inserting a pin or wire into a bone or other structure. The instrument may include a body, a first shaft, a second shaft, an actuator in communication with the second shaft, a first holding feature, and a second holding feature. Illustratively, the first shaft may include a lumen substantially concentric about a longitudinal axis of the first shaft. In some cases, the first shaft may be rotatable about the longitudinal axis and/or positioned at least partially within the body. The second shaft may be at least partially positioned around the first shaft and/or positioned at least partially within the body. In some cases, the second shaft may be axially mobile. The actuator may be actuated to move the second shaft in an axial direction with respect to (e.g., independent of) one or more of the first shaft and the body. The first holding feature may be located adjacent a first position along the longitudinal axis, where the first holding feature may be capable of passively applying a first force to an elongated member (e.g., a pin or wire) inserted into the lumen of the first shaft. The second holding feature may be capable of actively applying a second force to the elongated member inserted into the lumen of the first shaft.

In some illustrative instances, an instrument for facilitating the insertion of a pin or wire into a bone or other structure may include a body, a first shaft, a second shaft, one or more engagement features, a biasing mechanism, and an actuator member in communication with the second shaft. The first shaft may be positioned at least partially within the body and may include a lumen at least substantially concentric about a longitudinal axis of the first shaft. The second shaft may be positioned at least partially within the body and may be at least partially positioned around the first shaft. The one or more engagement features may extend at least partially into the lumen of the first shaft and may be capable of engaging an elongated member received in the lumen. The biasing mechanism may engage one or more of the one or more engagement features to automatically apply a force against an elongated member (e.g., a pin or wire) inserted into or received in the lumen of the first shaft. The actuator member may be actuated to longitudinally move the second shaft relative to (e.g., independent of or without longitudinal movement of) the first shaft to engage the second shaft with one or more of the one or more engagement features and selectively apply a force against the elongated member inserted into or received in the lumen of the first shaft.

In some instances, an instrument for facilitating the insertion of a pin or wire into a bone or other structure may be utilized in a method of maintaining an elongated member therewithin. In an example method, the instrument may receive an elongated member in a lumen of a rotatable first shaft thereof and may automatically apply a first force against the elongated member when the elongated member is received at and/or past a first position along a longitudinal axis of the lumen of the rotatable first shaft. The method may further include selectively applying a second force against the elongated member received in the lumen of the rotatable first shaft via axial movement of a rotatable second shaft of the instrument, where the axial movement may be relative to the rotatable first shaft.

The above summary of some example aspects is not intended to describe each disclosed embodiment or every implementation of the claimed disclosure.

BRIEF DESCRIPTION OF THE DRAWINGS

The disclosure may be more completely understood in consideration of the following detailed description of various embodiments in connection with the accompanying drawings, in which.

Figure 1:
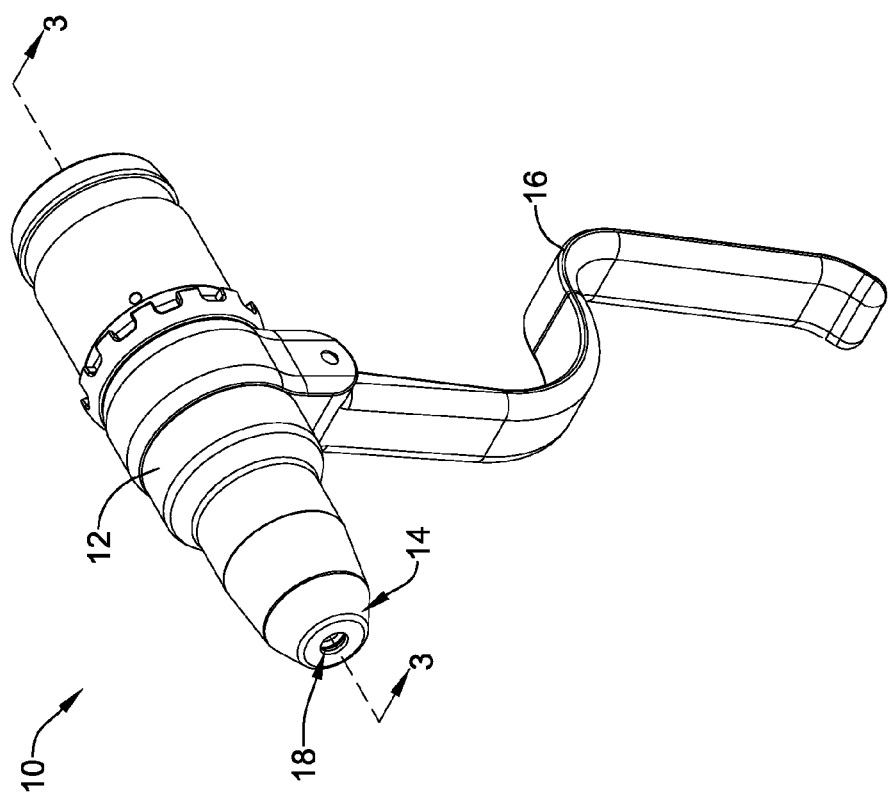
FIG. 1 is a schematic perspective view of an illustrative attachment apparatus for driving wires according to an aspect of the disclosure.

While the disclosure is amenable to various modifications and alternative forms, specifics thereof have been shown by way of example in the drawings and will be described in detail. It should be understood, however, that the intention is not to limit aspects of the claimed disclosure to the particular embodiments described. On the contrary, the intention is to cover all modifications, equivalents, and alternatives falling within the spirit and scope of the claimed disclosure.

DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used herein, the proximal end (e.g., trailing end) of an object is the end that is closest to the individual or instrument inserting the object during a medical procedure and the distal end (e.g., leading end) of an object is the end that is farthest from the individual or instrument inserting the object during a medical procedure.

As used herein, any numerical or other order designations of elements (e.g., first, second, third, a, b, c, etc.) are used for descriptive purposes to improve the clarity of the description of the disclosure and differentiate between similar disclosed features. These numerical indications, unless expressly indicated, are not used for any limiting purposes.

The following detailed description should be read with reference to the drawings in which similar elements in different drawings are numbered the same. The detailed description and the drawings, which are not necessarily to scale, depict illustrative embodiments and are not intended to limit the scope of the claimed disclosure. The illustrative embodiments depicted are intended only as exemplary. Selected features of any illustrative embodiment may be incorporated into an additional embodiment unless clearly stated to the contrary.

In some cases, pin wire driver attachments may facilitate driving and/or removing pins and wires by medical professionals during Total Knee Arthroplasty (TKA) procedures as well as other orthopedic or medical procedures and/or trauma. Some pin wire driver attachments may have variable grab points (e.g., grab points that may vary depending on pin or wire diameter), however, medical professionals appreciate a consistent grab point independent of wire size for consistency during procedures. Additionally, some pin wire driver attachments have a rotating outer nose, initial hold features set back a distance from the distal end of the pin wire driver attachment such that short pins (e.g., less than about 7-8 cm, or around 3 inches, may not receive an initial force applied thereto when received in the attachment), and manual adjustability to provide for various pin or wire diameters.

As disclosed herein a pin wire driver attachment 10 (e.g., and instrument) may have a nose that does not rotate and does not require manual adjustment for various pin or wire 26 diameters. The pin wire driver attachment 10 may provide one or more consistent grab points independent of wire diameter, for example, a passive hold feature may engage a received pin or wire 26 at 1 mm, 2 mm, 5 mm, 7 mm, 9 mm, 11 mm, 13 mm, 15 mm, 20 mm, 25 mm, 35 mm, etc., at about 1 mm, 2 mm, 5 mm, 7 mm, 9 mm, 11 mm, 13 mm, 15 mm, 20 mm, 25 mm, 35 mm, etc. and/or between 0 mm and 50 mm, between 1 and 35 mm, between 5 mm and 30 mm, between 10 mm and 25 mm, 10 mm and 20 mm, 10 mm and 15 mm, etc., or other distance from a distal end of the pin wire driver attachment 10. In some instances, a first pin wire driver attachment may be configured for a first set of pins or wires 26 having a diameter within a first range (e.g., less than about 3 mm, between 0.6 mm and 2.2 mm, or other similar range) and a second pin wire driver attachment may be configured for a second set of pins or wires 26 having a diameter within a second range (e.g., greater than about 2.0 mm, between 2.0 mm and 4.0 mm, or other similar range). Other pin wire driver attachments 10 may be configured to facilitate use with pins or wires 26 having diameters falling in one or more other ranges that may overlap or may be entirely separate from than the specified ranges.

Turning to the Figures, FIGS. 1-5 depict various views of an illustrative apparatus or pin wire driver attachment 10 for use with a hand piece 22 in a pin wire driver 24, where the Figures are provided merely for the purpose of illustrating features disclosed herein. As discussed, medical professionals (e.g., surgeons, etc.) may use pin wire drivers 24 to drive and/or remove pins and/or wires 26 during TKA procedures, as well as during other orthopedic procedures and/or trauma situations, and/or during other medical procedures.

Referring to FIG. 1, the pin wire driver attachment 10 is depicted having a body 12, a nose 14 of the body 12, and a handle 16. The attachment 10 may be removably couplable to the hand piece 22. The handle 16, by itself or in combination with one or more features, may be an actuator or actuator member, which when adjusted may actuate one or more features at least partially within the body 12. The nose 14 may include an opening 18 in communication with a lumen 30 (see FIGS. 3A and 3B) extending at least partially through the body 12, where the opening 18 may extend through a distal end of the nose 14 to the lumen 30 extending at least partially through the body 12. In some cases, the lumen 30 may extend entirely through the body 12.

Figure 2:
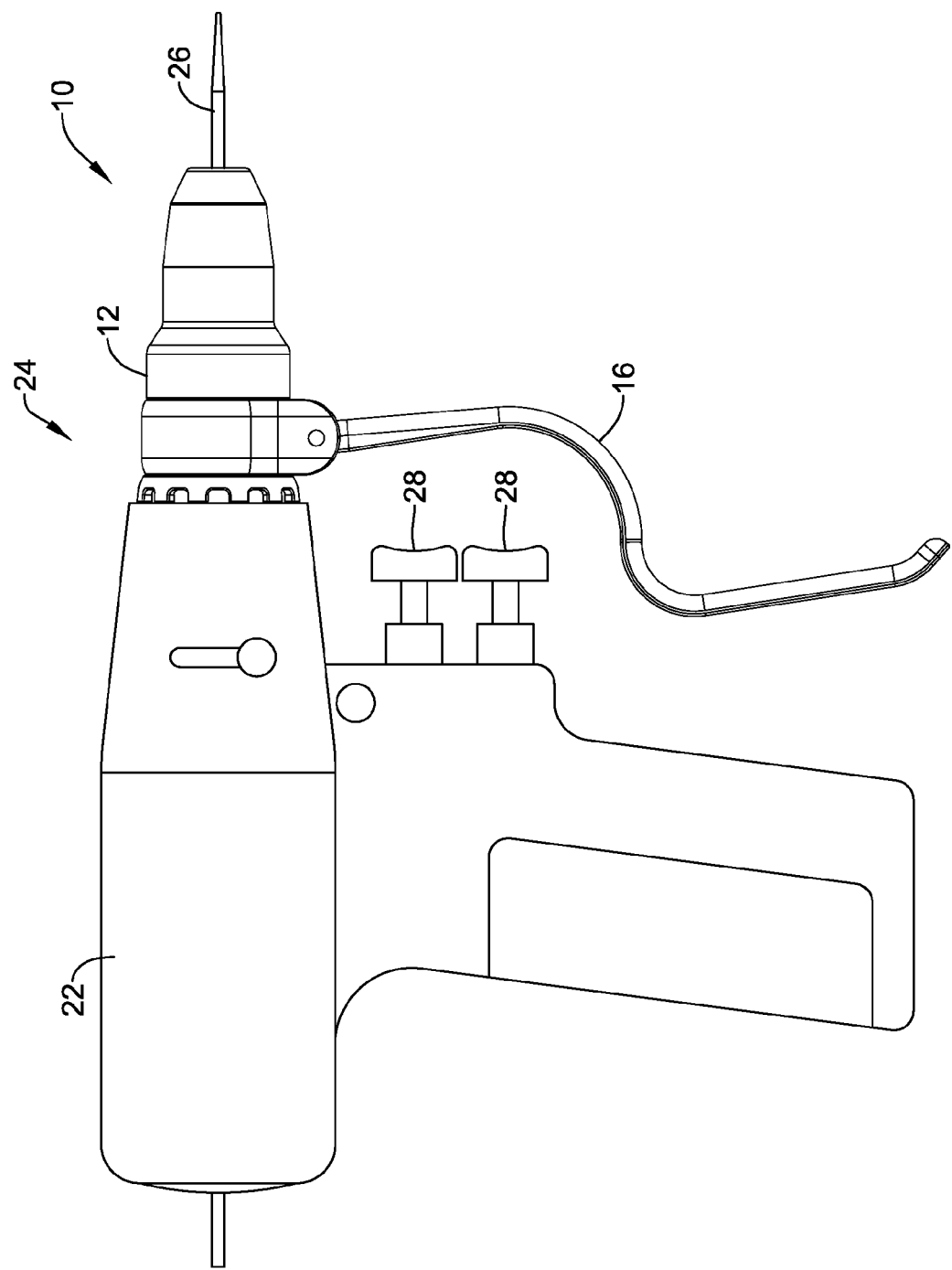
FIG. 2 is a schematic side view of an illustrative apparatus for driving wires according to an aspect of the disclosure.

The hand piece 22 of the pin wire driver 24 may include one or more triggers 28 (e.g., universal hand piece triggers, attachment specific hand piece triggers, or any other type of hand piece trigger), as shown in FIG. 2. For example, the hand piece 22 of the pin wire driver 24 may include one trigger 28, two triggers 28 (as shown in FIG. 2), three triggers 28, four triggers 28, or more triggers 28. In some instances, when there are two or more triggers 28, actuating a first one of the triggers 28 may cause rotation of a received pin or wire 26 in the clockwise direction and actuation of the other of the triggers 28 may cause rotation of the received pin or wire in the counter-clockwise direction. Alternatively, or in addition, the various triggers 28 may control the speed of rotation of a received pin or wire 26.

Figure 3A:
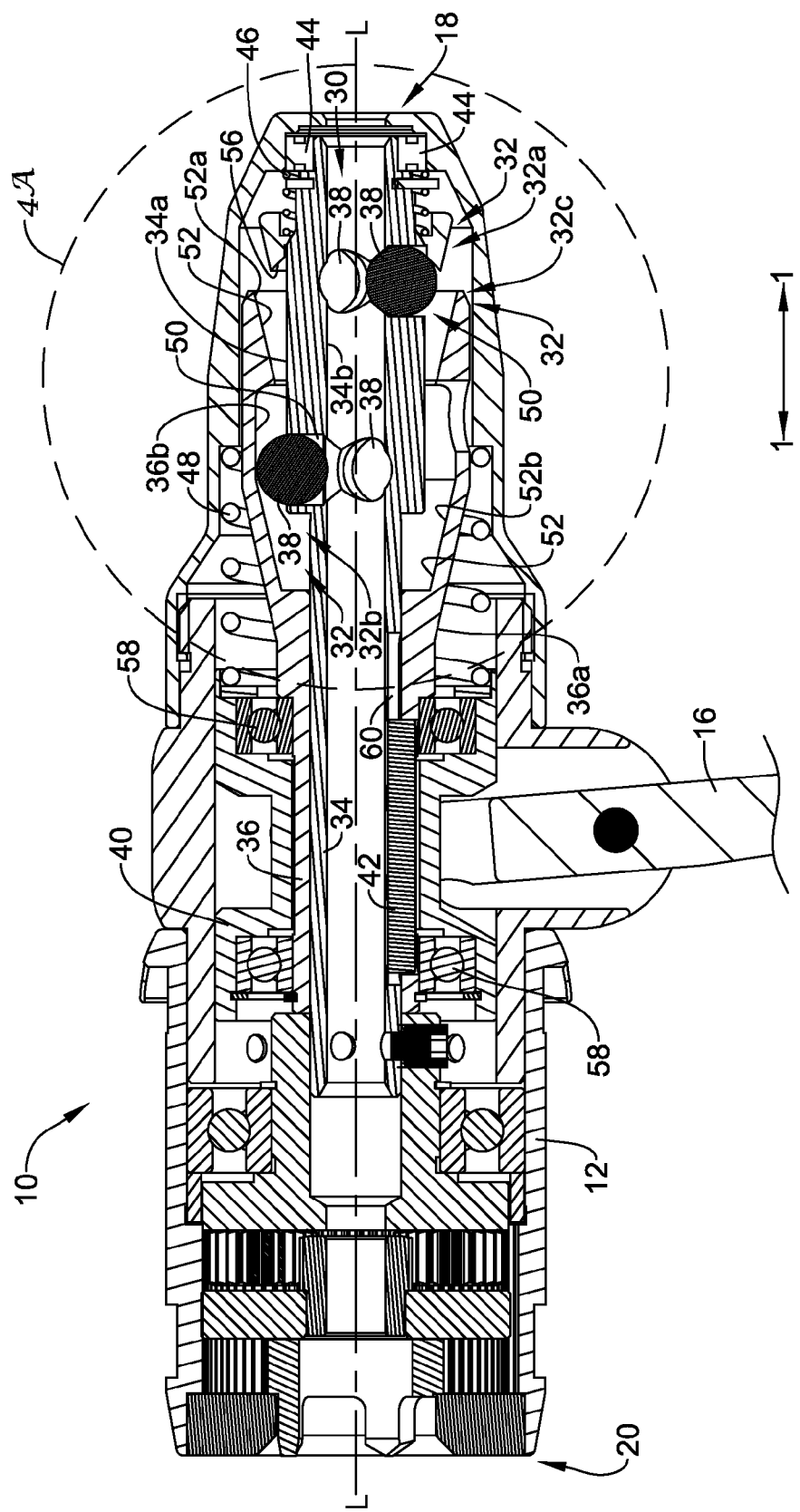
FIGS. 3A and 3B are schematic cross-sectional views of the attachment apparatus for driving wires depicted in FIG. 1, taken along line 3-3.
Figure 3B:
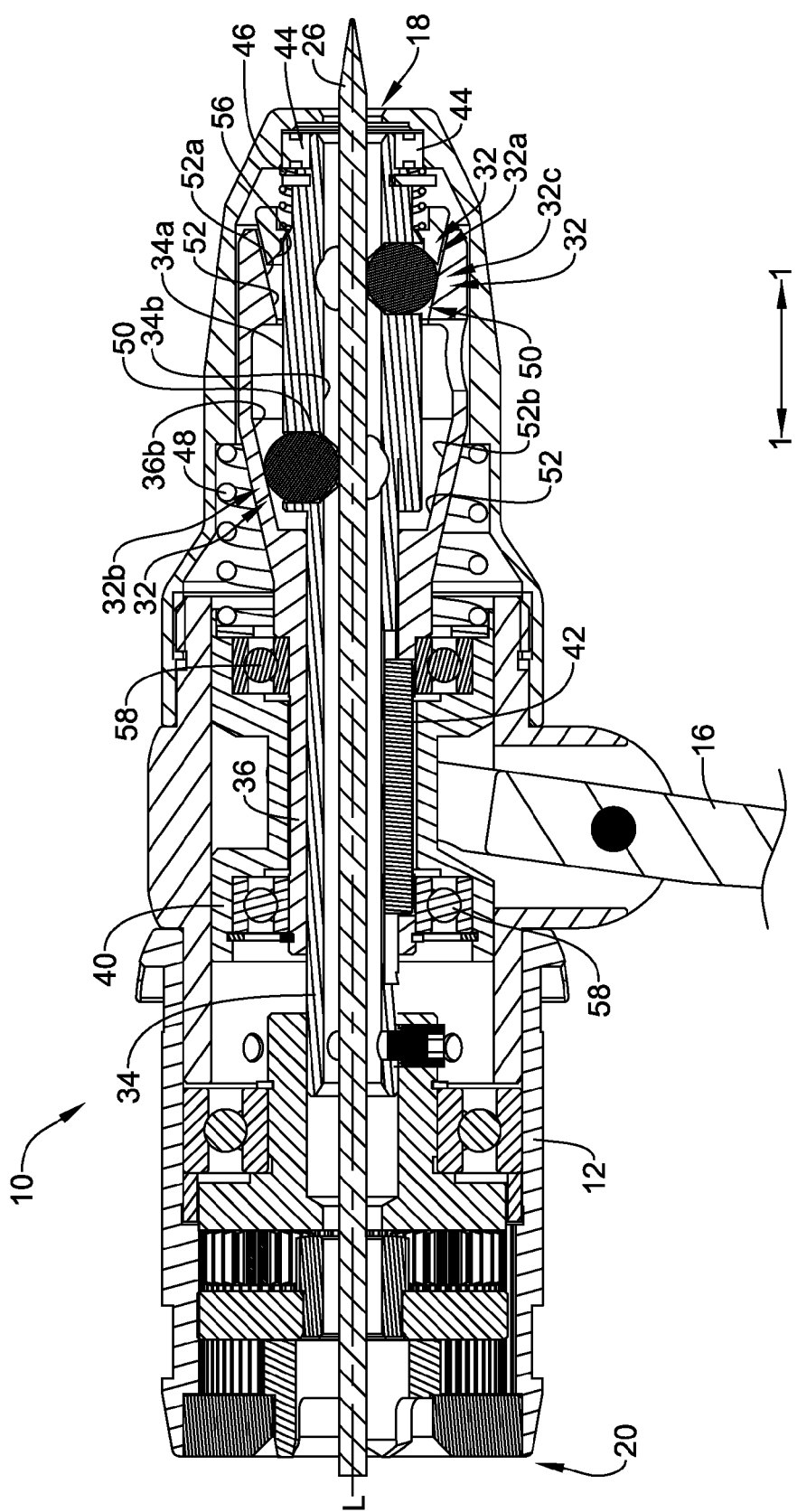

The body 12 of the pin wire driver attachment 10 may include gearing 20 configured to engage mating gears in a hand piece 22 of a pin wire driver 24. The gearing 20, as shown in FIGS. 3A and 3B, of the body 12 and/or the gearing of the hand piece 22 may be any type of gearing. In one example, the gearing 20 of the body 12 and the gearing of the hand piece 22 may be planetary gearing (e.g., two-stage planetary gearing or other planetary gearing) or any other type of gearing. Such gearing of the hand piece 22 may be caused to rotate in response to actuation of one or more of the triggers 28, which may in turn cause rotation of one or more features at least partially within the body 12 of the pin wire driver attachment 10.

The pin wire driver attachment 10 when connected to the hand piece 22 and/or when separated from the hand piece 22 may be capable of applying one or more similar or different forces to a pin or wire 26 received in a lumen 30 of thereof. In some illustrative instances, the pin wire driver attachment 10 may be capable of applying a force to a received or inserted pin or wire 26 at or adjacent each of one or more holding features 32.

In some cases, there may be more than two similar or dissimilar forces applied to the received or inserted pin or wire 26 at the two or more holding features 32 positioned along the lumen 30 of the pin wire driver attachment 10, where two or more of the two or more forces may be applied simultaneously with one another or at different times. For example, a first force may be applied to a received or inserted pin or wire 26 at a first holding feature 32a, a second force may be applied to the received or inserted pin or wire 26 at a second holding feature 32b, and/or a third force may be applied to the received or inserted pin or wire 26 at a third holding feature 32c, where one or more of the first, second, and/or third forces may be applied to the received pin or wire 26 simultaneously with one another or at different times. Although a first holding feature 32a, a second holding feature 32b, and a third holding feature 32c are labeled as such in FIGS. 3A and 3B, any holding feature 32 may be a first holding feature, a second holding feature, a third holding feature, and so on. The holding features 32 are further described below.

FIGS. 3A and 3B depict interior components or features of the pin wire driver attachment 10 taken along line 3-3 of FIG. 1 when the handle 16 is in a relaxed, neutral, spring biased, and/or natural position (FIG. 3A) and when the handle 16 is in an engaged and/or actuated position (FIG. 3B). The inner members or features of the pin wire driver attachment 10 may include, among other features, gearing 20, a first shaft 34, a second shaft 36, one or more engaging features 38 (e.g., ball bearings, other types of bearings, inserts, and/or other engaging features), plunger 40, a key 42, one or more stabilizing mechanisms 44 (e.g., bearings), and/or one or more other interior components or features. In some instances, the pin wire driver attachment 10 may be configured such that substantially all rotating parts of the pin wire driver attachment 10 are located within a body 12 thereof.

In some instances, the first shaft 34 may be a cannulated shaft with one or more at least partially rounded surfaces (e.g., at least partially rounded outer and/or inner surfaces). The lumen 30 may extend through the first shaft 34 and may be configured to receive the pin or wire 26 therethrough. The cannulated first shaft 34 may facilitate receiving any length pins or wires 26, as the open ends of the first shaft 34 will not limit a length of the received pin or wire 26.

Illustratively, the first shaft 34 may be at least partially positioned within the body 12 and may at least partially define the lumen 30 along longitudinal axis L-L. The first shaft 34 may be positioned substantially concentric about or around the longitudinal axis L-L and/or may be rotatable about the longitudinal axis L-L. In some cases, the first shaft 34 within the body 12 may be substantially stationary or stationary in the axial or longitudinal direction.

A distal end of the first shaft 34 may be positioned at or proximately proximal the opening 18 of the body 12. At or near the distal end of the first shaft 34, one or more stabilizing mechanisms 44 (e.g., one or more bearings) may provide a spacer between the body 12 and the outer surface 34a of the distal end of the first shaft 34. In one example, the stabilizing mechanism 44 may be a stabilizing bearing configured to support the first shaft 34 with respect to the body 12 and facilitate rotation of the first shaft 34 about the longitudinal axis L-L with respect to, relative to, or independent of the body 12.

In some instances, the first shaft 34 may include one or more openings 50 each for receiving an engaging feature 38 such as a spherical bearing or other engaging feature 38, where the one or more openings 50 may extend through the first shaft 34 from an outer surface 34a to an inner surface 34b of the first shaft 34. The one or more openings 50 for receiving engaging features 38 may be spaced (e.g., equally or unequally spaced) around the circumference of the first shaft 34 at one or more axially spaced locations. For example, as shown in FIGS. 3A and 3B, a first set of openings 50a are shown at a first axial position along the first shaft 34 and a second set of openings 50b are shown at a second axial position along the first shaft 34, where the second axial position along the first shaft 34 may be axially spaced from the first axial position. In the example, the openings 50 of each set of openings 50a and 50b may be circumferentially spaced (e.g., equally spaced or spaced otherwise) about the first shaft 34 and/or may include one, two, three (as shown in FIGS. 3A-4C), four, or more openings 50. Further, in the example, each opening 50 may receive a single engaging feature 38 (e.g., a ball bearing or other insert).

Illustratively, the engaging features 38 may be any feature having any size, where the engaging feature is capable of extending at least partially through an opening 50 in a wall of the first shaft 34 and into the lumen 30 and is capable of releasably engaging a received pin or wire 26 extending at least partially through the lumen 30. For example, the engaging features 38 may be ball bearings or other inserts. The engaging features 38 may have a diameter less than 5.0 mm, less than 10 mm, less than 15 mm, less than 20 mm, between 1 mm and 20 mm, 5 mm and 15 mm, 5 and 10 mm, or less than any other diameter such as, for example, a diameter of 1.0 mm, 1.5 mm, 2.0 mm, 2.5 mm, 3.0 mm, 3.5 mm, 4.0 mm, 4.5 mm, 5.0 mm, 5.5 mm, 6.0 mm, and so on, as desired.

In some instances, the engaging features 38 received within the distal most set of openings 50 (e.g., the first set of openings 50a, as shown in Figures) may be biased and/or urged radially inward toward the longitudinal axis L-L in a passive manner with a biasing mechanism. In one example, the biasing mechanism may include a spring 46 and a ramped or an angled hold feature 54 (e.g., a ring member having an angled or ramped surface 56 or other hold feature) that may be positioned at least partially within the body 12 and/or about the first shaft 34, such that the spring 46 may bias or urge the angled hold feature(s) 54 in an axial direction toward a set of openings 50 (e.g., a distal most set of openings, such as the first set of openings 50a) having engaging features 38 positioned therein to engage one or more of those engaging features 38 against the ramped surface 56 of the holding feature 54 and automatically apply a retention force against a pin or wire 26 received within or inserted into the lumen 30 of the first shaft 34. The angled hold feature(s) 54 may be configured to passively or automatically abut or engage engaging features 38 such that engaging features 38 may be biased radially inward toward the longitudinal axis L-L to automatically or passively engage a pin or wire 26 received within the lumen 30 of the first shaft 34.

In one instance, an angled or ramped surface 56 of the angled hold feature 54 may be configured such that the angled or ramped surface 56 abuts the engaging feature 38 and urges the engaging feature 38 radially inward toward the longitudinal axis L-L of the first shaft 34. Illustratively, the angled or ramped surface 56 of the angled hold feature 54 may be so configured such that the angled or ramped surface 56 may be at 40 degrees, at 45 degrees, at 50 degrees, between 35 degrees and 55 degrees, between 40 degrees and 50 degrees, or at or between other oblique angles with respect to the longitudinal axis L-L to urge the engaging features toward the longitudinal axis L-L.

Figure 4A:
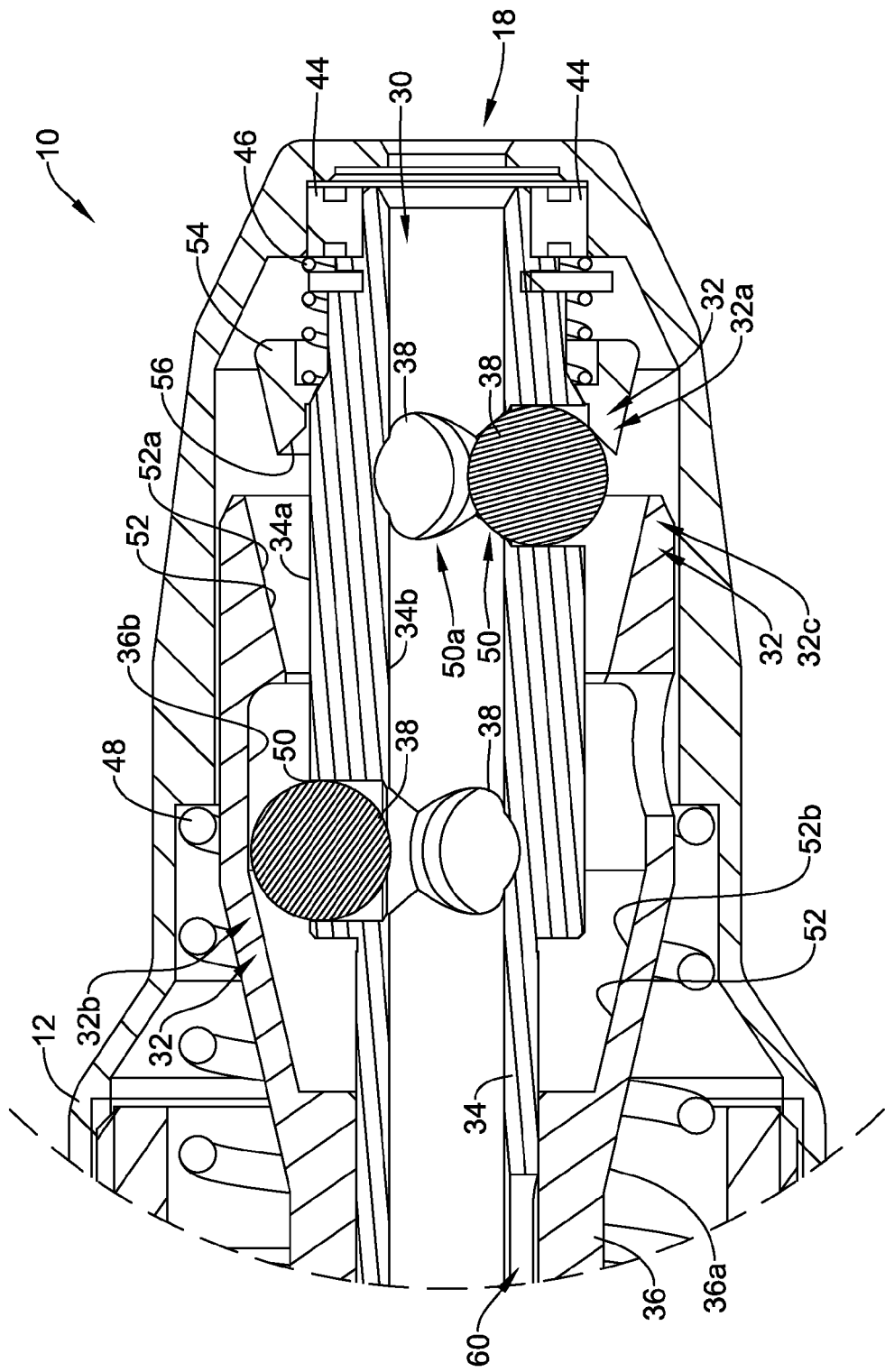
FIGS. 4A-4C are enlarged cross-sectional views of a portion of the attachment apparatus for driving wires depicted in FIG. 3A.
Figure 4B:
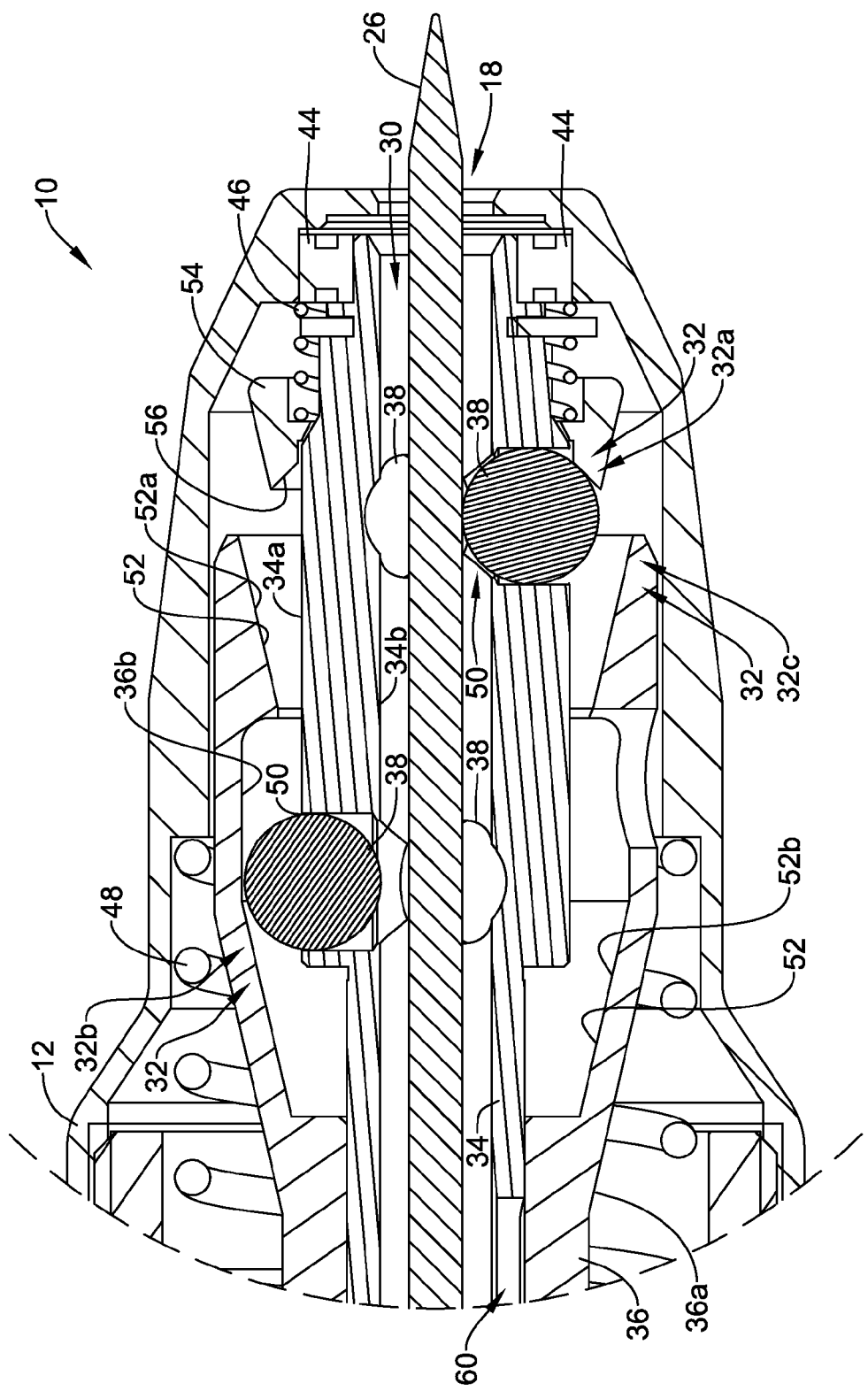

As the engaging features 38 of the distal most set of openings 50 may be biased toward the longitudinal axis L-L, these engaging features 38 may automatically and/or passively engage and/or hold a pin or wire 26 received within the lumen 30 of the first shaft 34 therein. The received pin or wire 26 may urge engaging features 38 away from the longitudinal axis L-L and the first spring 46 may counteract the force applied to the engaging features 38 by the pin or wire 26 to hold the pin or wire 26 within the body 12 of the pin wire driver attachment 10, as shown in FIG. 4B. The first spring 46 may have a spring constant that allows for insertion of the pin or wire 26 within the lumen 30 of the first shaft 34, but is also configured to apply force through the engaging features 38 to the received pin or wire 26 to passively hold the pin or wire 26 within the body 12.

The second shaft 36 may have one or more rounded surfaces (e.g., one or more at least partially rounded exterior surface 36a and/or one or more at least partially rounded interior surface 36b) and may be at least partially positioned around the first shaft 34 and at least partially positioned within the body 12 of the pin wire driver attachment 10, as shown in FIGS. 3A and 3B. Illustratively, the second shaft 36 may be positioned concentrically or otherwise around the longitudinal axis L-L and/or the first shaft 34. In some instances, the second shaft 36 may be rotatable about the longitudinal axis and/or may be axially movable and/or adjustable (e.g., axially movable and/or adjustable in the direction of arrows 1-1). A key 42 may be positioned between the first shaft 34 and the second shaft 36 in opening 60 such that the first shaft 34 rotates with the second shaft 36. Thus, the first shaft 34 may rotate as the second shaft 36 rotates and vice versa, while the second shaft is capable of axial or longitudinal movement independent of the first shaft 34.

In one example, the handle 16 may be in operative communication with the second shaft 36 such that actuation of the handle 16 and/or release of the handle 16 may result in axial movement of the second shaft 36 along the longitudinal axis L-L relative to the first shaft 34 and the body 12. The key 42, configured to create a rotating connection between the first shaft 34 and the second shaft 36, may be positioned and/or configured such that the second shaft 36 may rotate with the first shaft 34, but may be movable in the axial direction independent of the first shaft 34. For example, the key 42 may engage the second shaft 36 and may slidingly fit within an opening 60 of the first shaft 34, such that the second shaft 36 may move axially independent of movement of the first shaft 34 and may rotate with the first shaft 34.

In some instances, the second shaft 36 may have one or more angled or ramped surfaces 52. For example, the second shaft 36 have a first ramped surface 52a and a second ramped surface 52b, where the second ramped surface 52b may be axially spaced from the first ramped surface 52a. Although the second ramped surface 52b is depicted in FIGS. 3A and 3B as being located proximal the first ramped surface 52a, either ramped surface 52 may be labeled first or second ramped surface 52a, 52b. The first ramped surface 52a and/or the second ramped surface 52b may extend at least partially around the interior surface 36b at one or more spaced locations, or the first ramped surface 52a and/or the second ramped surface 52b may extend entirely around the interior surface 36b of the second shaft 36.

The interior surface 36b of the first ramped surface 52a and/or the interior surface 36b of the second ramped surface 52b may be configured to engage the one or more engaging features 38. In one example, the first and/or second ramped surfaces 52a, 52b may engage one or more of the engaging features 38 when the handle 16 is actuated causing the second shaft 36 to move axially in a distal direction and/or at one or more other times.

The first ramped surface 52a may be configured to engage a first set of engaging features 38 at a desired time with respect to when the second ramped surface 52b engages a second set of engaging features 38 as the handle 16 is actuated to cause the second shaft 36 to move axially and engage the engaging features 38. In one example, the first ramped surface 52a may engage a first set of engaging features 38 simultaneously with when the second ramped surface 52b engages a second set of engaging features 38 proximal the first set of engaging features 38 as the handle 16 is actuated. In another example, the first ramped surface 52a may engage a first set of engaging features 38 after the second ramped surface engages a second set of engaging features 38 proximal the first set of engaging features as the handle 16 is actuated.

When the interior surfaces 36b of the ramped surfaces 52 engage an engaging feature 38, the engaging feature 38 may be urged radially inward within the openings 50 of the first shaft 34 toward the longitudinal axis L-L about which the first shaft 34 is positioned. When a pin or wire 26 is positioned within the lumen 30 of the first shaft 34, the engaging features 38 may actively engage the pin or wire 26, as shown for example in FIGS. 3B and 4C, as the second shaft 36 is actuated distally.

The ramped surfaces 52 may be configured at any desired oblique angle with respect to the longitudinal axis L-L. Illustratively, the ramped surface 52 may be arranged at an angle of 40 degrees, of 45 degrees, of 50 degrees, between 35 degrees and 55 degrees, between 40 degrees and 50 degrees, or at or between other oblique angles with respect to the longitudinal axis L-L to urge the engaging features toward the longitudinal axis L-L.

In some instances, the handle 16 may engage or interact with a plunger 40 that may be positioned about and/or in communication with the second shaft 36. When the handle 16 is actuated, the plunger 40 may be engaged and moved axially to actuate movement of the second shaft 36 in the axial direction.

In some cases, one or more bearings 58 may be positioned between the second shaft 36 and the plunger 40. The bearings 58 may facilitate rotational movement of the second shaft 36 independent of the plunger 40. Illustratively, one, two, or more bearings 58 may be utilized to facilitate rotational movement between the second shaft 36 and the plunger 40, while allowing for axial movement of the second shaft 36 with axial movement of the plunger 40.

The plunger 40 and the second shaft 36 may be biased proximally in the axial direction by the second spring 48 to bias the angled or ramped surfaces 52 of the second shaft 36 away from engagement with one or more engagement features 38. In one example, the second spring 48 may extend between the body 12 or other feature in communication with the body 12 and the one or more features of the plunger 40 (as shown in FIGS. 3A and 3B) and the second shaft 36. When the handle 16 is actuated, the actuated handle 16 may interact with the plunger 40 to move the plunger 40 and/or the second shaft 36 axially in a distal direction against the bias of the second spring 48 to cause active engagement of the engaging features 38 with a received pin or wire 26. Alternatively, and in some instances, the second shaft 36, the plunger 40, the second spring 48, and/or the handle 16 may be configured such that the second shaft 36 may be biased in the distal direction and actuation of the handle 16 may cause proximal movement of the second shaft 36 with respect to the first shaft 34 and/or the body 12 to actively apply or to apply an active force to a pin or wire 26 received within the lumen 30 of the first shaft 34.

Figure 4C:
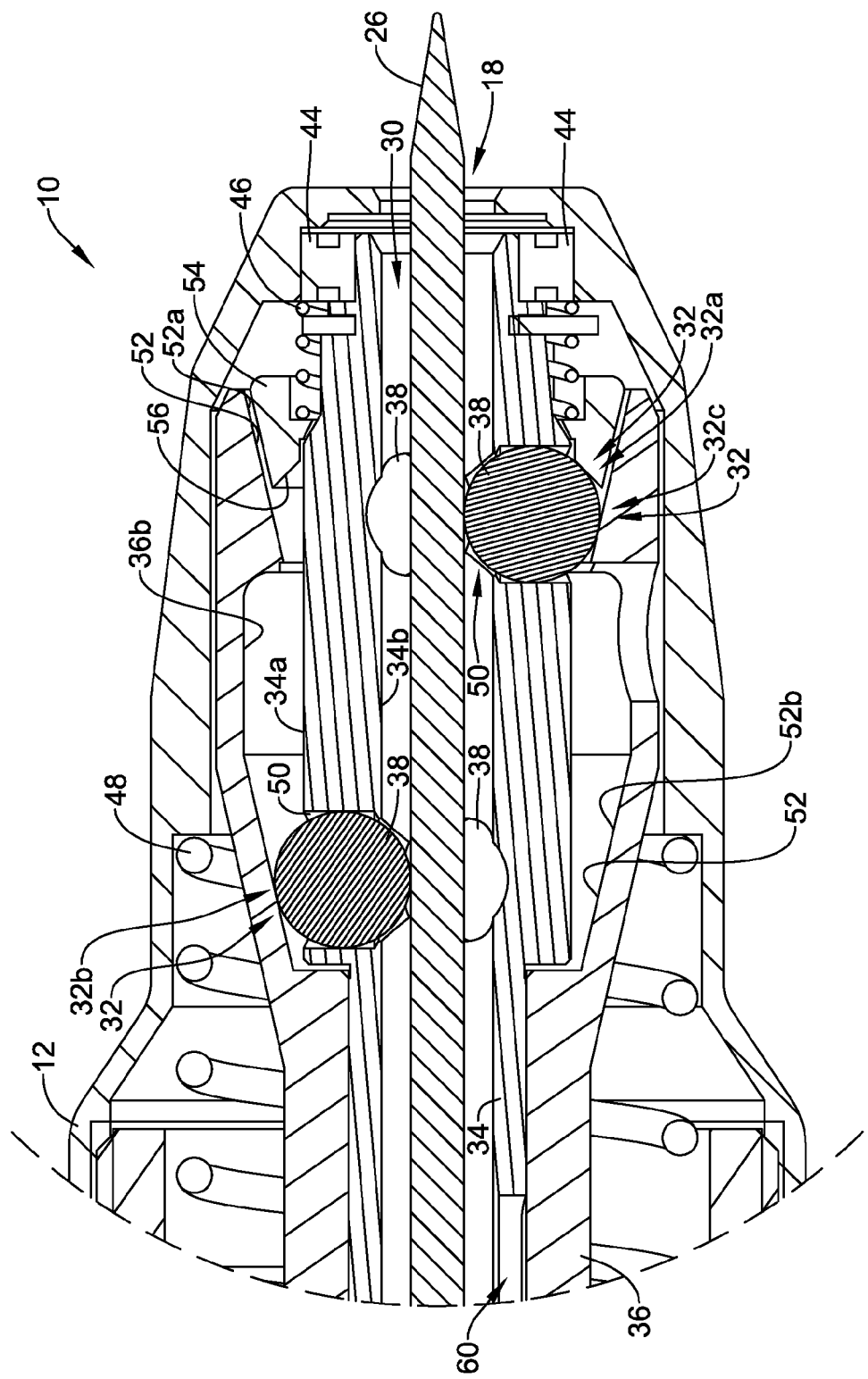
Figure 5:
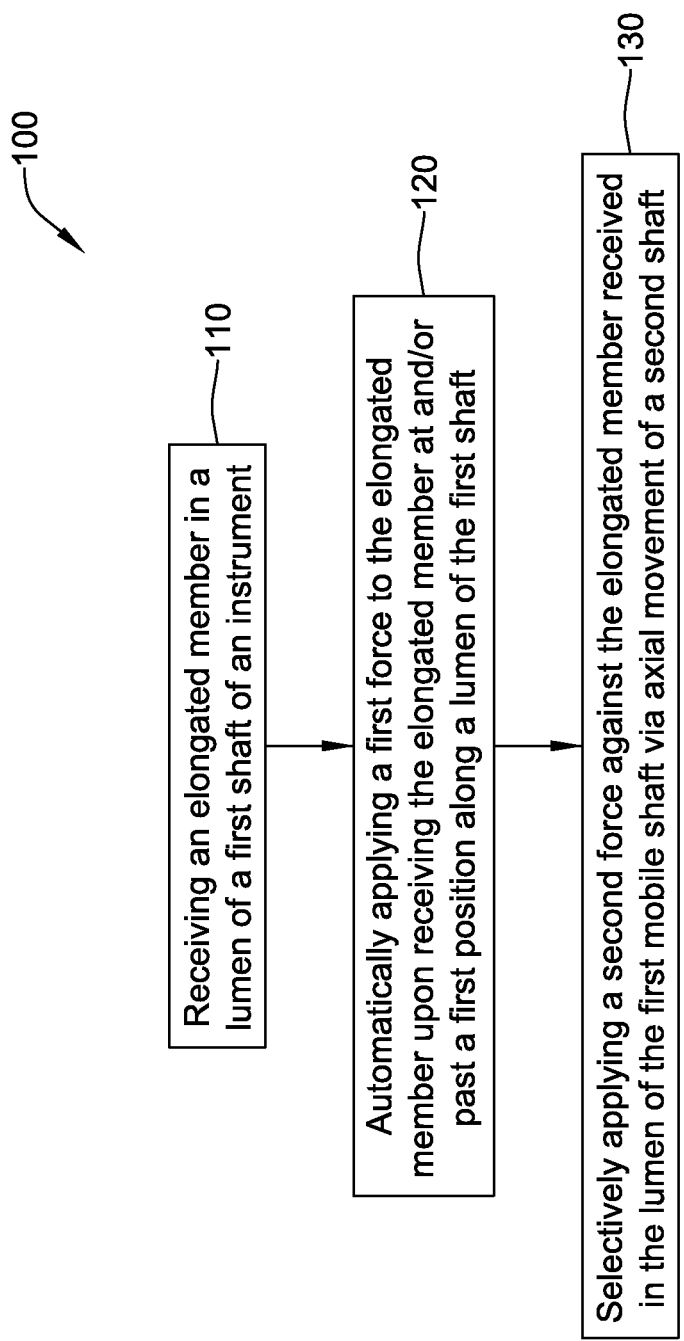
FIG. 5 is a schematic flow diagram of a method of using an illustrative attachment apparatus for driving wires according to an aspect of the disclosure.

The second spring 48 may have a spring constant that biases the plunger 40 and second shaft 36 axially in a proximal direction, where actuation of the handle 16 may overcome a force acting on the plunger 40 and/or the second shaft 36 to move the second shaft 36 in a proximal direction such that the second shaft 36 engages the engaging features 38 to apply an active force to a received pin or wire 26, as shown in FIG. 4C. The spring constant of the second spring 48 may operate to move the plunger 40 and/or the second shaft 36 axially in a proximal direction when the handle 16 is released to remove an active force being applied to the pin or wire 26 when the handle 16 is actuated. In some instances, the active force applied to a received pin or wire 26 during the actuation of the handle 16 may be greater than the passive force applied to the received pin or wire 26, where the passive force is substantially constantly applied to the received pin or wire 26 except when the active force is applied at the engaging features 38 in the set of openings 50 at which the passive force is applied to the received pin or wire 26.

In one or more alternative instances, the active force may be applied to a received pin or wire 26 in one or more manners that differ from the application of the active force described above. For example, the second shaft 36, the second spring 48, the engaging features 38, and/or other features may be configured to apply an active force to a received pin or wire 26 when in a natural, neutral, or relaxed position, and the handle 16 may be actuated to selectively remove the active force from the received pin or wire 26.

As discussed above, the pin wire driver attachment 10 may include holding features 32 to apply one or more passive and/or active forces to a pin or wire 26 received in the pin wire driver attachment 10. Holding features 32 as discussed herein may include one or more features utilized to either actively or passively engage a pin or wire 26 that is received within the lumen 30 of the first shaft 34. In some instances, the pin wire driver attachment 10 may include one or more holding features 32 that may apply a passive force to a received pin or wire 26 and one or more holding features 32 that may apply an active force to a received pin or wire 26. There may be any number of holding features 32, for example, there may be one holding feature, two holding features, three holding features, four holding features, or more holding features, if desired.

In one example, the pin wire driver attachment 10 may include two holding features 32. In such an instance a first holding feature 32a may be located a first position along the longitudinal axis L-L and/or may include a distal most set of engaging features 38 (e.g., one or more engaging features 38), an angled hold feature 54, a spring 46, and/or other features to constantly and/or passively (e.g., without actuation or releasing of a trigger, handle, or other mechanism) apply a force (e.g., a first force) to a pin or wire 26 received within the lumen 30 and extending to and/or beyond the first position along the longitudinal axis L-L. A second holding feature 32b may be located at a second position along the longitudinal axis L-L spaced proximally from the first position and/or at the first position along the longitudinal axis L-L. The second holding feature 32b may include a set of engaging features 38 (e.g., one or more engaging features 38) that are spaced proximally from the set of engaging features 38 of the first holding feature 32a or the engaging features 38 of the first holding feature 32, the second spring 48, and/or a ramped surface 52 of the second shaft 36 that may engage the set of engaging features 38 at the second position or first position along the longitudinal axis L-L to apply an active force or to actively apply a force (e.g., a second force) to the received pin or wire 26 at the second position or first position along the longitudinal axis L-L in response to actuating the handle 16.

As shown in FIGS. 3A-4C, the pin wire driver attachment 10 may include three holding features 32, where one holding feature may apply a passive force to a received pin or wire 26 and two holding features may apply an active force to the received pin or wire 26. Illustratively, a first holding feature 32a may be located at a first position along the longitudinal axis L-L and/or may include a distal most set of engaging features 38, an angled hold feature 54, a first spring 46, and/or other features to constantly and/or passively (e.g., without actuation of a trigger, handle, or other mechanism) apply a force (e.g., a first force) to a pin or wire 26 received within the lumen 30 and extending to and/or beyond the first position along the longitudinal axis L-L. A second holding feature 32b may be located at a second position along the longitudinal axis L-L and/or may include a set of engaging features 38 that are spaced proximally from the set of engaging features 38 of the first holding feature 32a, the second spring 48, and/or a ramped surface 52 (e.g., a second ramped surface 52b) of the second shaft 36 that may engage the set of engaging features 38 at the second position along the longitudinal axis L-L to apply an active force or to actively apply a force (e.g., a second force) to the received pin or wire 26 at the second position along the longitudinal axis L-L in response to actuating the handle 16. In some optional instances, a third holding feature 32c may be located at the first position along the longitudinal axis L-L and/or may include the set of engaging features 38 that are located at the first position along the longitudinal axis L-L, the second spring 48, and/or a ramped surface 52 (e.g., a first ramped surface 52a) of the second shaft 36 that may engage the set of engaging features 38 at the first position along the longitudinal axis L-L to apply an active force or to actively apply a force (e.g., a third force which many be equal to or different than the second force) to the received pin or wire 26 at the first position along the longitudinal axis L-L in response to actuating the handle 16.

In some instances, the first force, the second force, and the third force applied to a received pin or wire 26 may equal the same amount of force. Alternatively, one or more of the first force, the second force, and the third force may be different from at least one other of the first force, the second force, and the third force. In the example described above, the amount of force of the first force applied to the received pin or wire 26 may be less than the amount of force of each of the second force and the third force. In some instances, the amounts of the second force and the third force may be equal or may be different.

Any one of the holding features 32 may be numbered differently, for example, any holding feature 32 may be a first holding feature and any next holding feature 32 may be a second holding feature and any next holding feature 32 may be a third holding feature. The numbering of the holding features 32 and the numbering of any features herein described is done to distinguish between features and is not meant to be limiting in any way other than to indicate there is at least that many of those numbered features.

In some instances, a pin wire driver attachment 10 may be used in one or more methods. For example, the pin wire driver attachment 10 may be utilized in a method 100 of maintaining an elongated member in the pin wire driver attachment 10. The method 100 may include receiving a pin or wire 26 (e.g., an elongated member) in a lumen 30 of a rotatable first shaft 34 of the pin wire driver attachment 10. Upon receiving the pin or wire 26 at and/or past a first position along a longitudinal axis L-L of the lumen 30 of the first shaft 34, a first force may be automatically applied against the pin or wire 26 received in the lumen 30. A second force may be selectively applied against the pin or wire 26 received in the lumen 30 of the first shaft 34 of the pin wire driver attachment 10. In some instances, the second force may be selectively applied against the received pin or wire 26 via axial movement of a rotatable second shaft 36 of the pin wire driver attachment.

In some instances, the method 100 may include selectively applying a third force against the pin or wire 26 received in the lumen 30 of the first shaft 34 with the axial movement of the second shaft 36 that may or may not be used to apply the second force to the pin or wire 26. The first force and/or the second force may be applied to the pin or wire 26 at the first position along the longitudinal axis L-L. The third force may be applied to the pin or wire 26 at a second position along the longitudinal axis L-L. Illustratively, the second position along the longitudinal L-L axis may be spaced a distance proximal from the first position along the longitudinal axis of the first shaft 34. In some cases, the first position may be distal the second position so as to apply a passive force or automatic force to a received pin or wire 26 upon receiving only a portion of the pin or wire 26. Alternatively, or in addition, to the relative locations of the first and second positions discussed herein, the first and second positions, or other positions, may be located at any position relative to one another along the longitudinal axis L-L, as desired.

The second force and/or the third force may be applied to a received pin or wire 26 through actuation of the handle 16. When the handle 16 is in its natural or neutral position (e.g., when the handle is not actuated or no force acting from exterior the body 12 is applied to the handle 16), the plunger 40 and the second shaft 36 may be biased in the proximal direction by the second spring 48 or other spring mechanism and there is no active force acting on any of the engaging features 38 by the second shaft 36. When the handle 16 is actuated (e.g., when the handle is squeezed and/or a force is applied to the handle 16), the plunger 40 may be forced distally by the handle 16 against a biasing force of the second spring 48. When the plunger 40 is forced distally, the plunger 40 may cause the second shaft 36 to move distally toward the distal end of the pin wire driver attachment 10 to engage the engaging features 38. The more force that is applied to the handle 16 to actuate the handle, the greater the active force is that is applied to the received pin or wire 26 via the engagement of the engaging features 38 by the angled or ramped surfaces 52 of the second shaft 36.

As the second shaft 36 moves distally, the angled or ramped surfaces 52 of the second shaft 36 may engage one or more of the engaging features 38 applying an inward and/or compression force onto the received pin or wire 26 through the engaging features. In some cases, the interaction between the engaging features 38 and the angled or ramped surfaces 52 may be such that each engaging feature 38 of each set of engaging features 38 (e.g., each set may include three engaging features 38 equally spaced circumferentially around the first shaft 34 and each set may be positioned at different positions along the longitudinal axis L-L) applies the same amount of force to the received pin or wire 26 as the other engaging features 38 of its set. After the handle 16 has been actuated and a suitable active force has been applied to the received pin or wire 26, the triggers 28 of a hand piece 22 in communication with the pin wire driver attachment 10 may be actuated to rotate the pin or wire 26 that is securely held within the pin wire driver attachment 10.

Although certain steps of the method of operation may be discussed herein in one or more particular orders, it is contemplated one or more methods of operation may follow these steps in other orders (including a plurality of steps being performed simultaneously), may include one or more further steps, or may include further steps in any order.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. An instrument, the instrument comprising;
    a body;
    a first shaft having a lumen substantially concentric about a longitudinal axis, the first shaft being rotatable about the longitudinal axis and positioned at least partially within the body;
    a second shaft at least partially positioned around the first shaft and positioned at least partially within the body, the second shaft being axially mobile, the second shaft comprising:
        a first ramped surface; and
        a second ramped surface positioned a distance distal from the first ramped surface;
    an actuator member in communication with the second shaft;
    a first holding feature located adjacent a first position along the longitudinal axis, wherein the first holding feature is capable of passively applying a first force to an elongated member received in the lumen of the first shaft; and
    a second holding feature, where the second holding feature is capable of actively applying a second force to the elongated member received in the lumen of the first shaft.

2. The instrument of claim 1, wherein a third holding feature is capable of actively applying a third force to the elongated member.

3. The instrument of claim 2, wherein the third holding feature is positioned adjacent the first position along the longitudinal axis.

4. The instrument of claim 1, wherein the second holding feature is positioned adjacent the first position along the longitudinal axis.

5. The instrument of claim 1, where the second holding feature is positioned adjacent a second position along the longitudinal axis spaced longitudinally away from the first position.

6. The instrument of claim 1, wherein passively applying a first force to the elongated member includes automatically applying the first force to the elongated member upon receiving the elongated member at and/or past the first position along the longitudinal axis.

7. The instrument of claim 1, wherein the first holding feature comprises:
   one or more bearings capable of engaging the elongated member to apply the first force thereto;
   a ring member engaging the one or more bearings; and
   a spring engaging the ring member to bias the one or more bearings towards the longitudinal axis.

8. The instrument of claim 7, wherein the ring member includes a ramped surface for engaging the one or more bearings.

9. The instrument of claim 1, wherein the second holding feature comprises:
   one or more ball bearings positioned at least partially within the first shaft;
   a ramped surface of the second shaft for engaging the one or more ball bearings; and
   a spring biasing the second shaft away from engagement with the one or more ball bearings.

10. The instrument of claim 9, wherein the actuator member is configured to actuate engagement of the ramped surface of the second shaft with the one or more ball bearings.

11. The instrument of claim 1, further comprising:
    a first set of one or more ball bearings positioned at least partially within the first shaft;
    a second set of one or more ball bearings positioned a distance proximal from the first set of one or more ball bearings; and
    wherein:
       the first ramped surface is configured to engage the first set of one or more ball bearings to actively apply a force to the elongated member received in the lumen of the first shaft; and
       the second ramped surface is configured to engage the second set of one or more ball bearings to actively apply a force to the elongated member received in the lumen of the first shaft.

12. The instrument of claim 11, wherein the first ramped surface engages the first set of one or more ball bearings simultaneously with when the second ramped surface engages the second set of one or more ball bearings.

13. The instrument of claim 11, wherein the first ramped surface engages the first set of one or more ball bearings after the second ramped surface engages the second set of one or more ball bearings.

14. The instrument of claim 1, wherein the second shaft rotates about the longitudinal axis together with the first shaft rotating about the longitudinal axis.

15. The instrument of claim 1, wherein the second shaft is axially movable relative to the first shaft via actuation of the actuator member.

16. An instrument, the instrument comprising:
    a body;
    a first shaft having a lumen substantially concentric about a longitudinal axis, the first shaft positioned at least partially within the body;
    one or more engagement features extending at least partially into the lumen of the first shaft, the one or more engagement features comprising:
       a first set of engagement features; and
       a second set of engagement features extending at least partially into the lumen of the first shaft at a location proximal the first set of engagement features;
    a second shaft at least partially positioned around the first shaft and positioned at least partially within the body, the second shaft comprising:
       a first angled surface configured to engage the first set of engagement features upon actuation of the actuator member; and
       a second angled surface configured to engage the second set of engagement features upon actuation of the actuator member;
    a biasing mechanism configured to engage one or more of the one or more engagement features for automatically applying a force against an elongated member received in the lumen of the first shaft;
    an actuator member in communication with the second shaft, wherein actuation of the actuator member longitudinally moves the second shaft relative to the first shaft to engage the second shaft with the one or more engagement features to selectively apply a force against the elongated member received in the lumen of the first shaft.

17. The instrument of claim 16, wherein actuation of the actuator member engages the second shaft with the first set of engagement features and the second set of engagement features.

18. The instrument of claim 16, wherein the first angled surface of the second shaft is configured to engage the first set of engagement features after the second angled surface of the second shaft engages the second set of engagement features.

19. The instrument of claim 16, wherein the biasing mechanism comprises:
    a ramped hold feature having a ramped surface configured to engage the one or more engagement features; and
    a spring configured to bias the ramped surface against the one or more engagement features.

20. A method of maintaining an elongated member within an instrument, the method comprising:
    receiving an elongated member into a lumen of a rotatable first shaft of the instrument;
    automatically applying a first force against the elongated member upon receiving the elongated member at and/or past a first position along a longitudinal axis of the lumen of the rotatable first shaft;
    selectively applying a second force against the elongated member received in the lumen of the rotatable first shaft of the instrument with axial movement of a rotatable second shaft of the instrument;
    selectively applying a third force against the elongated member received in the lumen of the rotatable first shaft of the instrument with the axial movement of the rotatable second shaft of the instrument; and
    wherein:
       the first force and the second force are applied to the elongated member received in the lumen adjacent the first position along the longitudinal axis; and
    the third force is applied to the elongated member received in the lumen adjacent a second position along the longitudinal axis, the second position along the longitudinal axis is spaced a distance proximal from the first position along the longitudinal axis.

* * * * *